(12) United States Patent
Hochschuler et al.

(10) Patent No.: US 7,931,689 B2
(45) Date of Patent: Apr. 26, 2011

(54) METHOD AND APPARATUS FOR TREATING A VERTEBRAL BODY

(75) Inventors: Stephen Hochschuler, Dallas, TX (US); Wesley D. Johnson, Eden Prairie, MN (US); Kevin L. Nickels, Bloomington, MN (US); Thomas R. Hektner, Medina, MN (US); Larry Wales, Maplewood, MN (US); Tyler Lipschults, New Canaan, CT (US)

(73) Assignee: Spineology Inc., St. Paul, MN (US)

( * ) Notice: Subject to any disclaimer, the term of this patent is extended or adjusted under 35 U.S.C. 154(b) by 127 days.

(21) Appl. No.: 10/804,761

(22) Filed: Mar. 19, 2004

(65) Prior Publication Data

US 2004/0215343 A1   Oct. 28, 2004

Related U.S. Application Data

(63) Continuation of application No. 09/794,873, filed on Feb. 27, 2001, now Pat. No. 6,740,093.

(51) Int. Cl.
*A61F 2/44* (2006.01)
(52) U.S. Cl. ..................................... 623/17.12
(58) Field of Classification Search .............. 606/92–94, 606/61, 60, 246, 279; 623/17.11–17.12, 623/23.61–23.63
See application file for complete search history.

(56) References Cited

U.S. PATENT DOCUMENTS

| | | |
|---|---|---|
| 16,151 A | 2/1856 | Cole |
| 376,477 A | 1/1888 | Harcourt |
| 817,042 A | 4/1906 | Burns |
| 1,079,630 A | 11/1913 | Baum |
| 1,409,825 A | 3/1922 | Brush |
| 2,077,804 A | 4/1937 | Morrison |
| 2,677,369 A | 5/1954 | Knowles |
| 2,984,241 A | 5/1961 | Carlson |
| 3,030,951 A | 4/1962 | Mandarino |
| 3,426,364 A | 2/1969 | Lumb |
| 3,554,192 A | 1/1971 | Isberner |
| 3,628,524 A | 12/1971 | Jamshidi |
| 3,630,204 A | 12/1971 | Fishbein |
| 3,633,583 A | 1/1972 | Fishbein |
| 3,702,611 A | 11/1972 | Fishbein |
| 3,867,728 A | 2/1975 | Stubstad et al. |
| 3,875,595 A | 4/1975 | Froning |
| 3,902,498 A | 9/1975 | Niederer |
| 4,011,602 A | 3/1977 | Rybicki et al. |
| 4,013,071 A | 3/1977 | Rosenberg |

(Continued)

FOREIGN PATENT DOCUMENTS

DE    3509417 A1    9/1986

(Continued)

OTHER PUBLICATIONS

Bradley, S. and J.C., "The Use of Methylmethacrylate in the Treatment of Giant Cell Tumors of the Proximal Tiba", Aust. N.Z. Surg. vol. 49, No. 1, Feb. 1979, (3 pages).

(Continued)

*Primary Examiner* — Thomas C Barrett
*Assistant Examiner* — Michael J Araj
(74) *Attorney, Agent, or Firm* — Skaar Ulbrich Macari, P.A.

(57) ABSTRACT

An implantable container is used to stabilize or restore height in a vertebral body. After insertion the container is filled with a bone filler material such as bone cement.

9 Claims, 12 Drawing Sheets

U.S. PATENT DOCUMENTS

| | | | |
|---|---|---|---|
| 4,044,508 A | 8/1977 | Frederick | |
| 4,059,115 A | 11/1977 | Jumashev et al. | |
| 4,140,432 A | 2/1979 | Heule | |
| 4,162,867 A | 7/1979 | Calcaterra et al. | |
| 4,275,490 A | 6/1981 | Bivins | |
| 4,298,002 A | 11/1981 | Ronel et al. | |
| 4,309,777 A | 1/1982 | Patil | |
| 4,349,921 A | 9/1982 | Kuntz | |
| 4,369,769 A | 1/1983 | Edwards | |
| 4,379,451 A | 4/1983 | Getscher | |
| 4,401,112 A | 8/1983 | Rezaian | |
| 4,430,760 A | 2/1984 | Smestad | |
| 4,447,915 A | 5/1984 | Weber | |
| 4,457,028 A | 7/1984 | Draenert | |
| 4,468,200 A | 8/1984 | Münch | |
| 4,473,070 A | 9/1984 | Matthews et al. | |
| 4,479,491 A | 10/1984 | Martin | |
| 4,497,075 A | 2/1985 | Niwa et al. | |
| 4,501,269 A | 2/1985 | Bagby | |
| 4,545,374 A | 10/1985 | Jacobson | |
| 4,553,273 A | 11/1985 | Wu | |
| 4,554,914 A | 11/1985 | Kapp et al. | |
| 4,573,448 A | 3/1986 | Kambin | |
| 4,586,497 A | 5/1986 | Dapra et al. | |
| 4,589,414 A | 5/1986 | Yoshida et al. | |
| 4,596,243 A | 6/1986 | Bray | |
| 4,599,086 A | 7/1986 | Doty | |
| 4,603,194 A | 7/1986 | Mendiratta et al. | |
| 4,611,581 A | 9/1986 | Steffee | |
| 4,612,922 A | 9/1986 | Barber | |
| 4,636,217 A | 1/1987 | Ogilvie et al. | |
| 4,644,951 A | 2/1987 | Bays | |
| 4,646,738 A | 3/1987 | Trott | |
| 4,653,481 A | 3/1987 | Howland et al. | |
| 4,655,777 A | 4/1987 | Dunn et al. | |
| 4,657,550 A | 4/1987 | Daher | |
| 4,662,371 A | 5/1987 | Whipple et al. | |
| 4,686,997 A | 8/1987 | Oloff et al. | |
| 4,690,595 A | 9/1987 | Heule | |
| 4,696,292 A | 9/1987 | Heiple | |
| 4,714,469 A | 12/1987 | Kenna | |
| 4,714,478 A | 12/1987 | Fischer | |
| 4,716,893 A | 1/1988 | Fischer et al. | |
| 4,722,338 A | 2/1988 | Wright et al. | |
| 4,733,663 A | 3/1988 | Farley | |
| 4,735,625 A | 4/1988 | Davidson | |
| 4,743,256 A | 5/1988 | Brantigan | |
| 4,755,184 A | 7/1988 | Silverberg | |
| 4,756,649 A | 7/1988 | Heule | |
| 4,759,769 A | 7/1988 | Hedman et al. | |
| 4,772,287 A | 9/1988 | Ray et al. | |
| 4,777,948 A | 10/1988 | Wright | |
| 4,782,833 A | 11/1988 | Einhorn et al. | |
| 4,796,612 A | 1/1989 | Reese | |
| 4,834,752 A | 5/1989 | Van Kampen | |
| 4,834,757 A | 5/1989 | Brantigan | |
| 4,863,472 A | 9/1989 | Törmälä et al. | |
| 4,863,477 A | 9/1989 | Monson | |
| 4,865,604 A | 9/1989 | Rogozinski | |
| 4,874,389 A | 10/1989 | Downey | |
| 4,883,699 A | 11/1989 | Aniuk et al. | |
| 4,904,260 A | 2/1990 | Ray et al. | |
| 4,932,969 A | 6/1990 | Frey et al. | |
| 4,932,975 A | 6/1990 | Main et al. | |
| 4,936,848 A | 6/1990 | Bagby | |
| 4,969,888 A * | 11/1990 | Scholten et al. | 606/94 |
| 4,990,148 A | 2/1991 | Worrick, III et al. | |
| 5,015,255 A | 5/1991 | Kuslich | |
| 5,026,375 A | 6/1991 | Linovitz et al. | |
| 5,030,233 A | 7/1991 | Ducheyne | |
| 5,047,055 A | 9/1991 | Bao et al. | |
| 5,059,193 A | 10/1991 | Kuslich | |
| 5,061,269 A | 10/1991 | Muller | |
| 5,108,404 A | 4/1992 | Scholten et al. | |
| 5,108,438 A | 4/1992 | Stone | |
| 5,133,767 A | 7/1992 | Frey et al. | |
| 5,147,359 A | 9/1992 | Cozad et al. | |
| 5,147,360 A | 9/1992 | Dubousset | |
| 5,154,718 A | 10/1992 | Cozad et al. | |
| 5,171,280 A | 12/1992 | Baumgartner | |
| 5,171,281 A | 12/1992 | Parsons et al. | |
| 5,176,678 A | 1/1993 | Tsou | |
| 5,176,680 A | 1/1993 | Vignaud et al. | |
| 5,190,543 A | 3/1993 | Schlapfer | |
| 5,192,326 A | 3/1993 | Bao et al. | |
| 5,207,678 A | 5/1993 | Harms et al. | |
| 5,213,576 A | 5/1993 | Abiuso et al. | |
| 5,261,907 A | 11/1993 | Vignaud et al. | |
| 5,261,913 A | 11/1993 | Marnay | |
| 5,275,600 A | 1/1994 | Allard et al. | |
| 5,282,801 A | 2/1994 | Sherman | |
| 5,282,863 A | 2/1994 | Burton | |
| 5,303,718 A | 4/1994 | Krajicek | |
| 5,306,307 A | 4/1994 | Senter et al. | |
| 5,306,308 A | 4/1994 | Gross et al. | |
| 5,306,309 A | 4/1994 | Wagner et al. | |
| 5,306,310 A | 4/1994 | Siebels | |
| 5,306,311 A | 4/1994 | Stone et al. | |
| 5,312,407 A | 5/1994 | Carter | |
| 5,314,477 A | 5/1994 | Marnay | |
| 5,314,478 A | 5/1994 | Oka et al. | |
| 5,316,016 A | 5/1994 | Adams et al. | |
| 5,431,671 A | 7/1995 | Nallakrishnan | |
| 5,437,834 A | 8/1995 | Okimatsu et al. | |
| 5,451,227 A | 9/1995 | Michaelson | |
| 5,484,441 A | 1/1996 | Koros et al. | |
| 5,490,860 A | 2/1996 | Middle et al. | |
| 5,501,706 A | 3/1996 | Arenberg | |
| 5,503,164 A | 4/1996 | Friedman | |
| 5,514,157 A | 5/1996 | Nicholas et al. | |
| 5,531,791 A | 7/1996 | Wolfinbarger, Jr. | |
| 5,549,676 A | 8/1996 | Johnson | |
| 5,549,679 A | 8/1996 | Kuslich | |
| 5,556,429 A | 9/1996 | Felt | |
| 5,571,189 A | 11/1996 | Kuslich | |
| 5,649,947 A | 7/1997 | Auerbach et al. | |
| 5,653,713 A | 8/1997 | Michelson | |
| 5,653,761 A | 8/1997 | Pisharodi | |
| 5,674,295 A | 10/1997 | Ray et al. | |
| 5,716,416 A | 2/1998 | Lin | |
| 5,755,797 A * | 5/1998 | Baumgartner | 623/17.16 |
| 5,766,177 A | 6/1998 | Lucas-Dean et al. | |
| 5,782,832 A | 7/1998 | Larsen et al. | |
| 5,810,876 A | 9/1998 | Kelleher | |
| 5,817,119 A | 10/1998 | Klieman et al. | |
| 5,827,289 A | 10/1998 | Reiley et al. | |
| 5,827,328 A | 10/1998 | Buttermann | |
| 5,865,845 A | 2/1999 | Thalgott | |
| 5,865,848 A | 2/1999 | Baker | |
| 5,888,220 A | 3/1999 | Felt et al. | |
| 5,908,432 A | 6/1999 | Pan | |
| 5,919,235 A | 7/1999 | Husson et al. | |
| 5,961,531 A | 10/1999 | Weber et al. | |
| 5,961,554 A | 10/1999 | Janson et al. | |
| 5,968,098 A | 10/1999 | Winslow | |
| 5,972,015 A | 10/1999 | Scribner et al. | |
| 5,976,187 A | 11/1999 | Richelsoph | |
| 6,004,326 A | 12/1999 | Castro et al. | |
| 6,022,376 A | 2/2000 | Assell et al. | |
| 6,063,088 A | 5/2000 | Winslow | |
| 6,066,154 A | 5/2000 | Reiley et al. | |
| 6,083,225 A | 7/2000 | Winslow et al. | |
| 6,093,205 A | 7/2000 | McLeod et al. | |
| 6,110,210 A | 8/2000 | Norton et al. | |
| 6,110,211 A | 8/2000 | Weiss | |
| 6,113,638 A | 9/2000 | Williams et al. | |
| 6,127,597 A | 10/2000 | Beyar et al. | |
| 6,132,465 A | 10/2000 | Ray et al. | |
| 6,139,520 A | 10/2000 | McCrory et al. | |
| 6,142,997 A | 11/2000 | Michelson | |
| 6,146,419 A | 11/2000 | Eaton | |
| 6,146,422 A | 11/2000 | Lawson | |
| 6,156,067 A | 12/2000 | Bryan et al. | |
| 6,183,518 B1 | 2/2001 | Ross et al. | |
| 6,187,043 B1 | 2/2001 | Ledergerber | |
| 6,187,048 B1 | 2/2001 | Milner et al. | |
| 6,190,414 B1 | 2/2001 | Young et al. | |

| Patent | Date | Inventor |
|---|---|---|
| 6,193,757 B1 | 2/2001 | Foley et al. |
| 6,200,320 B1 | 3/2001 | Michelson |
| 6,206,930 B1 | 3/2001 | Burg et al. |
| 6,224,630 B1 | 5/2001 | Bao et al. |
| 6,235,043 B1 | 5/2001 | Reiley et al. |
| 6,241,734 B1 | 6/2001 | Scribner et al. |
| 6,241,769 B1 | 6/2001 | Nicholson et al. |
| 6,245,072 B1 | 6/2001 | Zdeblick et al. |
| 6,245,107 B1 | 6/2001 | Ferree |
| 6,248,110 B1 | 6/2001 | Reiley et al. |
| 6,248,131 B1 | 6/2001 | Felt et al. |
| 6,267,763 B1 | 7/2001 | Castro |
| 6,280,456 B1 | 8/2001 | Scribner et al. |
| 6,283,998 B1 | 9/2001 | Eaton |
| 6,296,632 B1 | 10/2001 | Lüscher et al. |
| 6,299,590 B1 | 10/2001 | Lüscher et al. |
| 6,306,177 B1 | 10/2001 | Felt et al. |
| 6,332,882 B1 | 12/2001 | Zucherman et al. |
| 6,332,894 B1 | 12/2001 | Stalcup et al. |
| 6,358,251 B1 | 3/2002 | Mirza |
| 6,379,355 B1 | 4/2002 | Zucherman et al. |
| 6,379,690 B2 | 4/2002 | Blanchard et al. |
| 6,383,188 B2 | 5/2002 | Kuslich et al. |
| 6,383,190 B1 | 5/2002 | Preissman |
| 6,395,031 B1 | 5/2002 | Foley et al. |
| 6,395,034 B1 | 5/2002 | Suddaby |
| 6,402,750 B1 | 6/2002 | Atkinson et al. |
| 6,413,278 B1 | 7/2002 | Marchosky |
| 6,419,676 B1 | 7/2002 | Zucherman et al. |
| 6,419,677 B2 | 7/2002 | Zucherman et al. |
| 6,423,083 B2 | 7/2002 | Reiley et al. |
| 6,425,919 B1 | 7/2002 | Lambrecht |
| 6,425,923 B1 | 7/2002 | Stalcup et al. |
| 6,428,576 B1 | 8/2002 | Haldimann |
| 6,436,143 B1 | 8/2002 | Ross et al. |
| 6,443,988 B2 | 9/2002 | Felt et al. |
| 6,451,020 B1 | 9/2002 | Zucherman et al. |
| 6,478,796 B2 | 11/2002 | Zucherman et al. |
| 6,482,233 B1 | 11/2002 | Aebi et al. |
| 6,482,234 B1 | 11/2002 | Weber et al. |
| 6,482,235 B1 | 11/2002 | Lambrecht et al. |
| 6,500,178 B2 | 12/2002 | Zucherman et al. |
| 6,500,205 B1 | 12/2002 | Michelson |
| 6,508,839 B1 | 1/2003 | Lambrecht et al. |
| 6,514,256 B2 | 2/2003 | Zucherman et al. |
| 6,540,747 B1 | 4/2003 | Marino |
| 6,558,386 B1 | 5/2003 | Cragg |
| 6,558,390 B2 | 5/2003 | Cragg |
| 6,565,606 B1 | 5/2003 | Bruce et al. |
| 6,575,978 B2 | 6/2003 | Peterson et al. |
| 6,575,979 B1 | 6/2003 | Cragg |
| 6,582,446 B1 | 6/2003 | Marchosky |
| 6,589,199 B1 | 7/2003 | McCrory et al. |
| 6,592,625 B2 | 7/2003 | Cauthen |
| 6,595,995 B2 | 7/2003 | Zdeblick et al. |
| 6,602,291 B1 | 8/2003 | Ray et al. |
| 6,607,544 B1 | 8/2003 | Boucher et al. |
| 6,613,054 B2 | 9/2003 | Scribner et al. |
| 6,620,196 B1 | 9/2003 | Trieu |
| 6,623,505 B2 | 9/2003 | Scribner et al. |
| 6,629,947 B1 | 10/2003 | Sahatjian et al. |
| 6,632,247 B2 | 10/2003 | Boyer, II et al. |
| 6,649,030 B1 | 11/2003 | Tesar |
| 6,652,527 B2 | 11/2003 | Zucherman et al. |
| 6,652,534 B2 | 11/2003 | Zucherman et al. |
| 6,652,584 B2 | 11/2003 | Michelson |
| 6,660,038 B2 | 12/2003 | Boyer, II et al. |
| 6,663,647 B2 | 12/2003 | Reiley et al. |
| 6,666,893 B2 | 12/2003 | Burg et al. |
| 6,679,886 B2 | 1/2004 | Weikel et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,709,458 B2 | 3/2004 | Michelson |
| 6,712,819 B2 | 3/2004 | Zucherman et al. |
| 6,716,216 B1 | 4/2004 | Boucher et al. |
| 6,716,247 B2 | 4/2004 | Michelson |
| 6,726,691 B2 | 4/2004 | Osorio et al. |
| 6,740,090 B1 | 5/2004 | Cragg et al. |
| 6,740,093 B2 | 5/2004 | Hochschuler et al. |
| 6,746,485 B1 | 6/2004 | Zucherman et al. |
| 6,749,614 B2 | 6/2004 | Teitelbaum et al. |
| 6,749,635 B1 | 6/2004 | Bryan |
| 6,758,849 B1 | 7/2004 | Michelson |
| 6,764,512 B2 | 7/2004 | Keller |
| 6,783,546 B2 | 8/2004 | Zucherman et al. |
| 6,790,210 B1 | 9/2004 | Cragg et al. |
| 6,793,679 B2 | 9/2004 | Michelson |
| 6,796,983 B1 | 9/2004 | Zucherman et al. |
| 6,800,092 B1 | 10/2004 | Williams et al. |
| 6,805,695 B2 | 10/2004 | Keith et al. |
| 6,805,697 B1 | 10/2004 | Helm et al. |
| 6,814,756 B1 | 11/2004 | Michelson |
| 6,821,277 B2 | 11/2004 | Teitelbaum |
| 6,833,006 B2 | 12/2004 | Foley et al. |
| 6,835,205 B2 | 12/2004 | Atkinson et al. |
| 6,835,208 B2 | 12/2004 | Marchosky |
| 6,849,092 B2 | 2/2005 | Van Dyke et al. |
| 6,852,095 B1 | 2/2005 | Ray |
| 6,869,445 B1 | 3/2005 | Johnson |
| 6,875,212 B2 | 4/2005 | Shaolian et al. |
| 6,883,520 B2 | 4/2005 | Lambrecht et al. |
| 6,893,466 B2 | 5/2005 | Trieu |
| 6,899,713 B2 | 5/2005 | Shaolian et al. |
| 6,899,716 B2 | 5/2005 | Cragg |
| 6,899,719 B2 | 5/2005 | Reiley et al. |
| 6,902,566 B2 | 6/2005 | Zucherman et al. |
| 6,921,403 B2 | 7/2005 | Cragg et al. |
| 6,923,813 B2 | 8/2005 | Phillips et al. |
| 6,936,072 B2 | 8/2005 | Lambrecht et al. |
| 6,949,105 B2 | 9/2005 | Bryan et al. |
| 6,962,606 B2 | 11/2005 | Michelson |
| 6,964,667 B2 | 11/2005 | Shaolian et al. |
| 6,964,674 B1 | 11/2005 | Matsuura et al. |
| 6,969,404 B2 | 11/2005 | Ferree |
| 6,972,035 B2 | 12/2005 | Michelson |
| 6,974,478 B2 | 12/2005 | Reiley et al. |
| 6,981,981 B2 | 1/2006 | Reiley et al. |
| 6,984,247 B2 | 1/2006 | Cauthen |
| 6,986,788 B2 | 1/2006 | Paul et al. |
| 6,997,956 B2 | 2/2006 | Cauthen |
| 7,001,431 B2 | 2/2006 | Bao et al. |
| 7,004,970 B2 | 2/2006 | Cauthen III et al. |
| 7,008,424 B2 | 3/2006 | Teitelbaum |
| 7,008,453 B1 | 3/2006 | Michelson |
| 7,014,659 B2 | 3/2006 | Boyer, II et al. |
| 7,025,771 B2 | 4/2006 | Kuslich et al. |
| 7,029,473 B2 | 4/2006 | Zucherman et al. |
| 7,033,395 B2 | 4/2006 | Cauthen |
| 7,044,954 B2 | 5/2006 | Reiley et al. |
| 7,052,516 B2 | 5/2006 | Cauthen, III et al. |
| 7,077,865 B2 | 7/2006 | Bao et al. |
| 7,087,058 B2 | 8/2006 | Cragg |
| 7,087,082 B2 | 8/2006 | Paul et al. |
| 7,087,084 B2 | 8/2006 | Reiley |
| 7,087,087 B2 | 8/2006 | Boyer, II et al. |
| 7,094,258 B2 | 8/2006 | Lambrecht et al. |
| 7,101,375 B2 | 9/2006 | Zucherman et al. |
| 7,114,501 B2 | 10/2006 | Johnson et al. |
| 7,118,598 B2 | 10/2006 | Michelson |
| 7,124,761 B2 | 10/2006 | Lambrecht et al. |
| 7,147,665 B1 | 12/2006 | Bryan et al. |
| 7,153,307 B2 | 12/2006 | Scribner et al. |
| 7,156,877 B2 | 1/2007 | Lotz et al. |
| 7,179,262 B2 | 2/2007 | Bryan et al. |
| 7,189,234 B2 | 3/2007 | Zucherman et al. |
| 7,189,235 B2 | 3/2007 | Cauthen |
| 7,198,047 B2 | 4/2007 | Lambrecht et al. |
| 7,201,751 B2 | 4/2007 | Zucherman et al. |
| 7,204,851 B2 | 4/2007 | Trieu et al. |
| 7,220,281 B2 | 5/2007 | Lambrecht et al. |
| 7,226,481 B2 | 6/2007 | Kuslich |
| 7,234,468 B2 | 6/2007 | Johnson et al. |
| 7,258,692 B2 | 8/2007 | Thelen et al. |
| 7,258,700 B2 | 8/2007 | Lambrecht et al. |
| 7,270,658 B2 | 9/2007 | Woloszko et al. |
| 7,273,497 B2 | 9/2007 | Ferree |
| 7,300,440 B2 | 11/2007 | Zdeblick et al. |

| | | |
|---|---|---|
| 7,300,465 B2 | 11/2007 | Paul et al. |
| 7,309,338 B2 | 12/2007 | Cragg |
| 7,318,823 B2 | 1/2008 | Sharps et al. |
| 7,331,956 B2 | 2/2008 | Hovda et al. |
| RE40,156 E | 3/2008 | Sharps et al. |
| 7,338,526 B2 | 3/2008 | Steinberg |
| 7,357,798 B2 | 4/2008 | Sharps et al. |
| 7,387,625 B2 | 6/2008 | Hovda et al. |
| 7,393,351 B2 | 7/2008 | Woloszko et al. |
| 7,427,284 B2 | 9/2008 | Seedhom et al. |
| 7,449,021 B2 | 11/2008 | Underwood et al. |
| 7,455,672 B2 | 11/2008 | Michelson |
| 7,462,178 B2 | 12/2008 | Woloszko et al. |
| 7,473,268 B2 | 1/2009 | Zucherman et al. |
| 7,476,226 B2 | 1/2009 | Weikel et al. |
| 7,485,119 B2 | 2/2009 | Thelen et al. |
| 7,488,329 B2 | 2/2009 | Thelen et al. |
| 7,491,219 B2 | 2/2009 | Steinberg |
| 7,491,236 B2 | 2/2009 | Cragg et al. |
| 7,497,868 B2 | 3/2009 | Steinberg |
| 7,503,936 B2 | 3/2009 | Trieu |
| 7,507,243 B2 | 3/2009 | Lambrecht et al. |
| 7,510,567 B2 | 3/2009 | Zucherman et al. |
| 7,513,911 B2 | 4/2009 | Lambrecht et al. |
| 7,520,900 B2 | 4/2009 | Trieu |
| 7,524,333 B2 | 4/2009 | Lambrecht et al. |
| 7,534,254 B1 | 5/2009 | Michelson |
| 7,547,317 B2 | 6/2009 | Cragg |
| 7,547,324 B2 | 6/2009 | Cragg et al. |
| 7,553,329 B2 | 6/2009 | Lambrecht et al. |
| 7,553,330 B2 | 6/2009 | Lambrecht et al. |
| 7,563,282 B2 | 7/2009 | Lambrecht et al. |
| 7,569,056 B2 | 8/2009 | Cragg et al. |
| 7,582,106 B2 | 9/2009 | Teitelbaum et al. |
| 7,601,174 B2 | 10/2009 | Kelly et al. |
| 7,608,077 B2 | 10/2009 | Cragg et al. |
| 7,608,106 B2 | 10/2009 | Reiley |
| 7,608,107 B2 | 10/2009 | Michelson |
| 7,618,461 B2 | 11/2009 | Trieu |
| 7,621,939 B2 | 11/2009 | Zucherman et al. |
| 7,621,950 B1 | 11/2009 | Globerman et al. |
| 7,635,378 B2 | 12/2009 | Zucherman et al. |
| 7,641,658 B2 | 1/2010 | Shaolian et al. |
| 7,641,692 B2 | 1/2010 | Bryan et al. |
| 7,655,042 B2 | 2/2010 | Foley et al. |
| 7,658,765 B2 | 2/2010 | Lambrecht et al. |
| 7,662,173 B2 | 2/2010 | Cragg et al. |
| 7,670,379 B2 | 3/2010 | Cauthen |
| 7,682,364 B2 | 3/2010 | Reiley et al. |
| 7,691,145 B2 | 4/2010 | Reiley et al. |
| 7,699,877 B2 | 4/2010 | Davison |
| 7,704,256 B2 | 4/2010 | Sand et al. |
| 7,708,742 B2 | 5/2010 | Scribner et al. |
| 7,713,301 B2 | 5/2010 | Bao et al. |
| 7,717,958 B2 | 5/2010 | Cragg et al. |
| 7,717,961 B2 | 5/2010 | Lambrecht et al. |
| 7,722,530 B2 | 5/2010 | Davison |
| 7,727,262 B2 | 6/2010 | Shaolian et al. |
| 7,727,263 B2 | 6/2010 | Cragg |
| 7,731,720 B2 | 6/2010 | Sand et al. |
| 7,744,599 B2 | 6/2010 | Cragg |
| 7,749,225 B2 | 7/2010 | Chappuis et al. |
| 7,749,228 B2 | 7/2010 | Lieberman |
| 7,749,267 B2 | 7/2010 | Karmon |
| 7,749,273 B2 | 7/2010 | Cauthen, III et al. |
| 7,749,275 B2 | 7/2010 | Lambrecht et al. |
| 7,753,941 B2 | 7/2010 | Keith et al. |
| 7,758,619 B2 | 7/2010 | Zucherman et al. |
| 7,766,965 B2 | 8/2010 | Bao et al. |
| 7,771,431 B2 | 8/2010 | Scribner et al. |
| 7,771,482 B1 | 8/2010 | Karmon |
| 2001/0034526 A1 | 10/2001 | Kuslich et al. |
| 2002/0022856 A1 | 2/2002 | Johnson et al. |
| 2002/0026195 A1 | 2/2002 | Layne et al. |
| 2002/0032447 A1 | 3/2002 | Weikel et al. |
| 2002/0045942 A1 | 4/2002 | Ham |
| 2002/0058947 A1 | 5/2002 | Hochschuler et al. |
| 2002/0068974 A1 | 6/2002 | Kuslich et al. |
| 2002/0156531 A1 | 10/2002 | Felt et al. |
| 2003/0033017 A1 | 2/2003 | Lotz et al. |
| 2004/0073308 A1 | 4/2004 | Kuslich |
| 2004/0092933 A1 | 5/2004 | Shaolian et al. |
| 2004/0215344 A1 | 10/2004 | Hochschuler et al. |
| 2006/0149379 A1 | 7/2006 | Kuslich et al. |
| 2008/0086133 A1 | 4/2008 | Kuslich et al. |
| 2010/0152855 A1 | 6/2010 | Kuslich |

FOREIGN PATENT DOCUMENTS

| | | |
|---|---|---|
| DE | 4409836 A1 | 9/1995 |
| EP | 0277282 A1 | 8/1988 |
| EP | 0 322 334 | 6/1989 |
| EP | 0 480 954 | 6/1990 |
| EP | 0 621 020 | 3/1994 |
| EP | 0 621 020 A1 | 10/1994 |
| FR | 2 639 823 | 12/1988 |
| FR | 2 639 823 | 6/1990 |
| FR | 2 662 073 | 11/1991 |
| FR | 2 714 590 | 7/1995 |
| WO | WO 89/09030 A1 | 10/1989 |
| WO | WO 91/00713 A1 | 1/1991 |
| WO | WO 93/16664 | 9/1993 |
| WO | WO 99/02214 A1 | 1/1999 |
| WO | WO 01/21246 | 3/2001 |
| WO | WO 03/07854 A1 | 1/2003 |

OTHER PUBLICATIONS

Campanacci, M., Gui, L. and Savini, R., "Godoli, The Treatment of Tinial Plateau Fractures", Chi. Org. Mov. 72(3), Dec. 1975 (Italian text (pp. 234-256) English translation.

Kyphon Surgical Technique Manual, 1999, (pp. 5,6,9,16-19).

Kyphon Vertebral Treatment Notebook, date unknown, (9 pages).

Kyphon web page, www.kyphon.com, Mar. 13, 2001, (2 pages).

AOM Techniques Manual, date unknown, (11 pages).

Garfin, Steven R., Yuan, Hansen A., Reiley, Mark A., "New Technologies in Spine-Kyphoplasty and Vertebroplasty for the Treatment of Painful Osteoporotic Compression Fractures", Spine, vol. 26, No. 14, pp. 1511-1514, 2001.

Lieberman, I.H., Dudeney, S., Reinhardt, M.,K., and Bell, G., "Initial Outcome and Efficacy of "Kyphoplasty" in the Treatment of Painful Osteoporatic Vertebral", Spine, vol. 26, No. 14, pp. 1631-1638, 2001.

Application and File History of U.S. Patent No. 5,549,679, issued Aug. 27, 1996, Inventor Stephen D. Kuslich.

Application and File History for U.S. Patent No. 6,740,093, issued May 25, 2004, Inventors Hochschuler et al.

Application and File History for U.S. Appl. No. 09/909,667, filed Jul. 20, 2001, Inventors Kuslich et al., www.uspto.gov.

Application and File History for U.S. Appl. No. 10/804,955, filed Mar. 19, 2004, Inventors Hochschuler et al.

Judgement—Request for Adverse—Bd.R. 127(b), Patent Interference No. 105,252, dated Apr. 11, 2005.

Application and File History for U.S. Appl. No. 09/827,202 (now U.S. Patent No. 6,575,978), filed Apr. 5, 2001, Inventors Peterson et al.

Application and File History for U.S. Appl. No. 12/503,663, filed Jul. 15, 2009, Inventors Kuslich.

Application and File History for U.S. Provisional Appl. No. 60/219,853, filed Jul. 21, 2000, Inventor Kuslich.

Application and File History for U.S. Provisional Appl. No. 60/185,323, filed Feb. 28, 2000, Inventor Hochschuler.

Application and File History for U.S. Provisional Appl. No. 60/239,217, filed Oct. 10, 2000, Inventor Johnson.

Application and File History for U.S. Provisional Appl. No. 60/239,216, filed Oct. 10, 2000, Inventor Johnson.

Application and File History for U.S. Provisional Appl. No. 10/440,036 (now U.S. Patent No. 7,226,481), filed May 16, 2003, Inventor Kuslich.

Application and File History for U.S. Provisional Appl. No. 11/282,910, filed Nov. 18, 2005, Inventor Kuslich.

Application and File History for U.S. Provisional Appl. No. 11/906,755, filed Oct. 3, 2007, Inventor Kuslich.

Application and File History for U.S. Provisional Appl. No. 12/624,179, filed Nov. 23, 2009, Inventor Kuslich.

Application and File History for U.S. Provisional Appl. No. 60/220,303, filed Jul. 24, 2000, Inventor Hektner.

Application No. PCT/US01/22837, filed Jul. 20, 2001, Applicant The Spineology Group, LLC, International Search Report dated Mar. 8, 2002, 1 page.

Patent Interference No. 105,252, *Kuslich et al.* v. *Hochschuler et al.*, Documents Dated Nov. 9, 2004-Feb. 3, 2005.

Application and File History for U.S. Appl. No. 07/350,126 (now U.S. Patent No. 5,015,255), filed May 10, 1989, Inventor Kuslich.

Application and File History for U.S. Appl. No. 08/246,959 (now U.S. Patent No. 5,571,189), filed May 20, 1994, Inventor Kuslich.

Application and File History for U.S. Appl. No. 09/782,176 (now U.S. Patent No. 6,383,188), filed Feb. 13, 2001, Inventors Kuslich et al.

* cited by examiner

METHOD AND APPARATUS FOR TREATING A VERTEBRAL BODY

CROSS-REFERENCE TO RELATED CASES

This application is a continuation of co-pending application Ser. No. 09/794,873, filed on Feb. 27, 2001, now U.S. Pat. No. 6,740,093 which claims the benefit of the following Provisional Applications: "Cavity Sealing Barrier", Ser. No. 60/185,323, filed Feb. 28, 2000; "Implant for Hard Bones", Ser. No. 60/220,303, filed Jul. 24, 2000; "Vertebral Body Sealing Device and Method", Ser. No. 60/239,216, filed Oct. 10, 2000; "Hydraulic Distraction with Permeable Membrane", Ser. No. 60/239,217, filed Oct. 10, 2000 and incorporates each of these by reference in their entirety.

FIELD OF THE INVENTION

The present invention relates generally to the treatment of bones and more particularly to the treatment of the vertebral bodies found in the human spine.

BACKGROUND OF THE INVENTION

The human spine consists of a complex set of interrelated anatomic elements including a set of bones called vertebral bodies. Intervertebral discs separate most vertebral bodies. These discs includes a "spongy" nucleus pulpous surrounded by an annulus fibrosis "membrane". The annulus fibrosis connects the opposed endplates of adjacent vertebral bodies. All of these structures together with muscles act to provide motion, stability and protection for the spine. When healthy, these structures effectively protect the spinal cord and allow for normal motion.

However there are many disease states and aging processes that impact the patient. Osteoporosis and metastatic disease reduce the structural integrity of the vertebral bodies, predisposing them to fracture. Vertebral fractures can lead to loss of vertebral height which can exacerbate existing neurological condition or it can predispose the spine to other symptoms. Back pain often results from these conditions. Vertebroplasty is an effort to stabilize these fractures and to alleviate this source of pain.

Generally, fractures and loss of height if not treated results in a cascade of injury which is undesirable. For this reason various efforts have been directed at stabilizing and restoring the natural vertebral bodies of the back. Efforts have also been directed to replacing the vertebral bodies. condition or it can predispose the spine to other symptoms. Back pain often results from these conditions. Vertebroplasty is an effort to stabilize these fractures and to alleviate this source of pain.

Generally, fractures and loss of height if not treated results in a cascade of injury which is undesirable. For this reason various efforts have been directed at stabilizing and restoring the natural vertebral bodies of the back. Efforts have also been directed to replacing the vertebral bodies.

U.S. Pat. No. 5,108,404 to Scholten et al among others teaches a technique for height restoration that uses a bone cement product introduced into a cavity after a cavity has been made with an inflatable device. One problem with this system is the extravasation of bone cement to sensitive areas. Another problem is the difficulty of obtaining consistent control of height restoration with the Scholten system.

SUMMARY

In contrast to the prior art, the present invention involves both a container device that is permanently implanted and a method of using the container to stabilize the vertebral body or to restore height to the vertebral body.

In one embodiment the container is porous to the bone filler material. In another embodiment the container is impermeable to the bone filler material. In each embodiment the container controls and regulates the delivery of bone filler material into the vertebral body.

In one embodiment the container is flexible and conformal to the cavity. In another embodiment the container has a fixed shape which conforms to the cavity shape when deployed.

In one embodiment of the method, the bone filler is injected until the cavity is completely filled stabilizing the vertebral body. In another embodiment of the method the bone filler is injected and displaces the endplates of the vertebral body "restoring height" through a hydraulic jacking effect and stabilizing their vertebral body.

There are numerous bone filler materials which can be used to fill the container including bone cement and other materials. However it is a general property of the bone fillers that they must be injectable in a fluid state and that they harden.

BRIEF DESCRIPTION OF THE DRAWINGS

Throughout the several views of the drawings there are shown illustrative embodiments of the inventions in which like reference numerals indicate equivalent or identical structure, wherein.

DETAILED DESCRIPTION

The various container devices and the methods for using the container devices are disclosed in the context of the treatment of vertebral bodies. It should be recognized that the inventions may be used in other bones which present the same or similar pathologies, including but not limited to tibial plateaus, distal radius fractures, calcaneous fractures.

Figure 1:
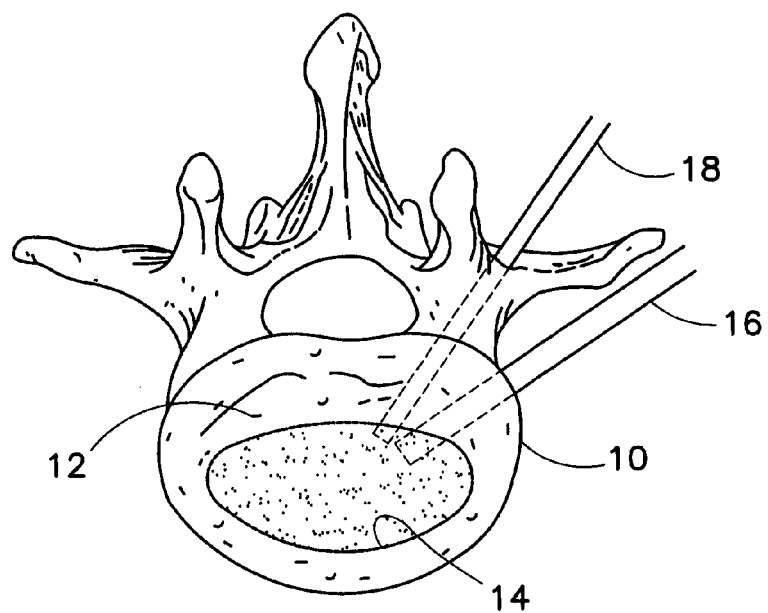
FIG. 1 is a sectional view of a vertebral body.
Figure 2:
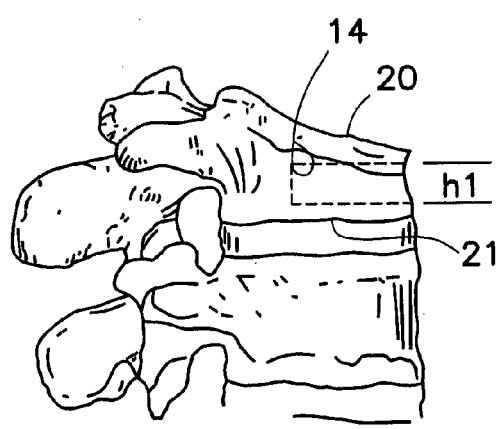
FIG. 2 is a view of a vertebral body in elevation.
Figure 3:
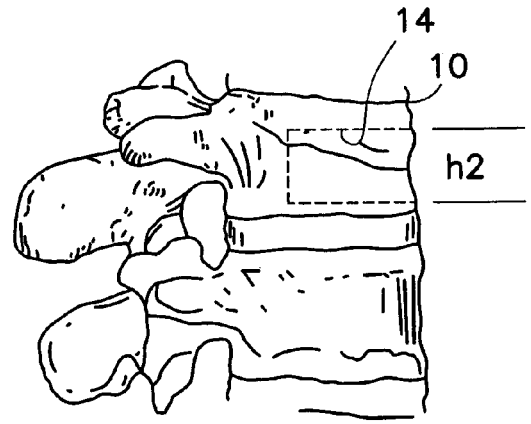
FIG. 3 is a view of a vertebral body in elevation.

FIG. 1, FIG. 2 and FIG. 3 taken together are intended to show a cavity creation process that precedes treatment with the devices and methods of the invention. In general cavity creation techniques are well known and they may include the creation of a cavity with a balloon device as is known in the art.

FIG. 1 shows a vertebral body 10 in partial cross section. The exterior portion of the vertebra is dense cortical bone and the interior is porous cancellous bone which is labeled 12 in the figure. The cavity 14 is depicted by the dashed outline in the drawing and it is formed in the porous bone. The shape of the cavity depends on the technique used to form it. This cavity is made in a conventional way. For example a tool may be introduced through extra-pedicular access tube 16 or trans-pedicular access tube 18 and operated in the vertebral body. As seen in the drawing the extrapedicular access tube 16 may have a larger diameter and will be preferred by some surgeons. In general, the access approach for cavity creation will also be used for the introduction of the devices of the invention. These approaches will be used for the methods of the invention.

FIG. 2 shows a collapsed vertebral body 10 in elevation with a compression fracture and associated loss of height. The superior endplate 20 has moved due to a fracture and normal loading. The nominal height of the cavity formed in this vertebral body is labeled "h1" in the figure. As the end plate moves the angle formed between the superior endplate 20 and the inferior endplate 21 becomes acute which is undesirable. In the extreme case both sides of the endplates fall to form a severely compressed rectangular shaped vertebral body.

FIG. 3 shows a fractured vertebral body that requires intervention. In this vertebral body the height of the cavity 14 is indicated by the nominal height of the vertebral body labeled as "h2" in the figure.

Taken together the FIGS. 1, 2 and 3 represent the formation of a cavity 14 prior to treatment with device of the present invention.

Figure 4:
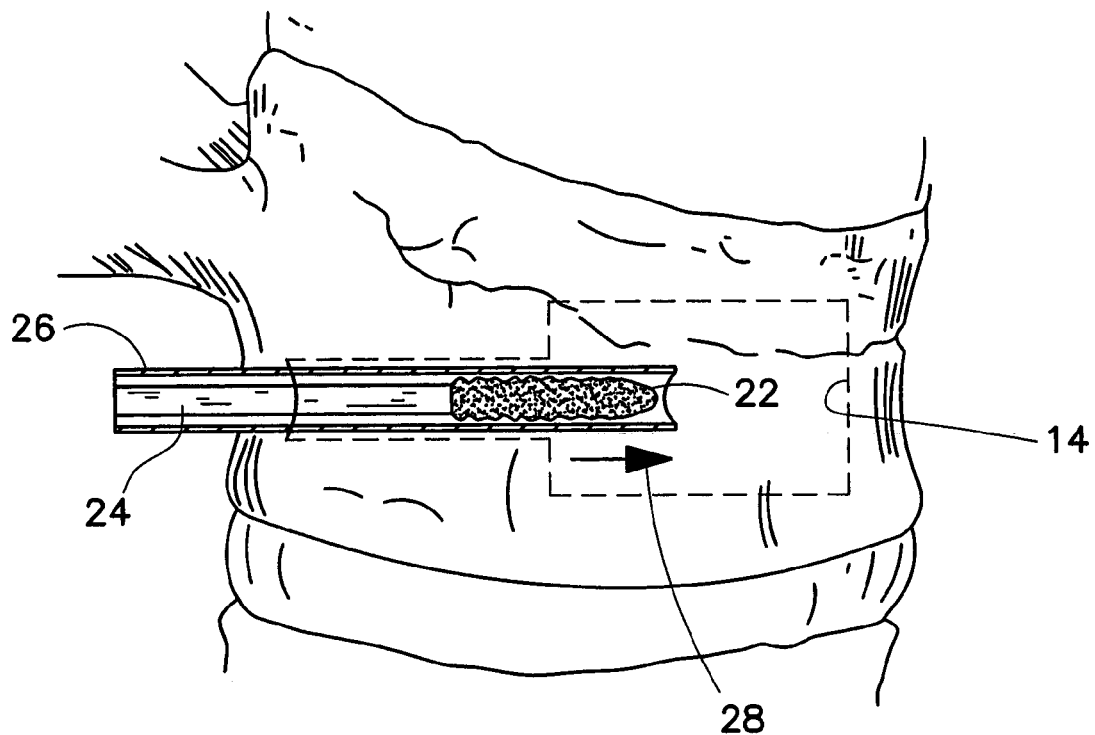
FIG. 4 is a view of a vertebral body with items shown in phantom view.
Figure 5:
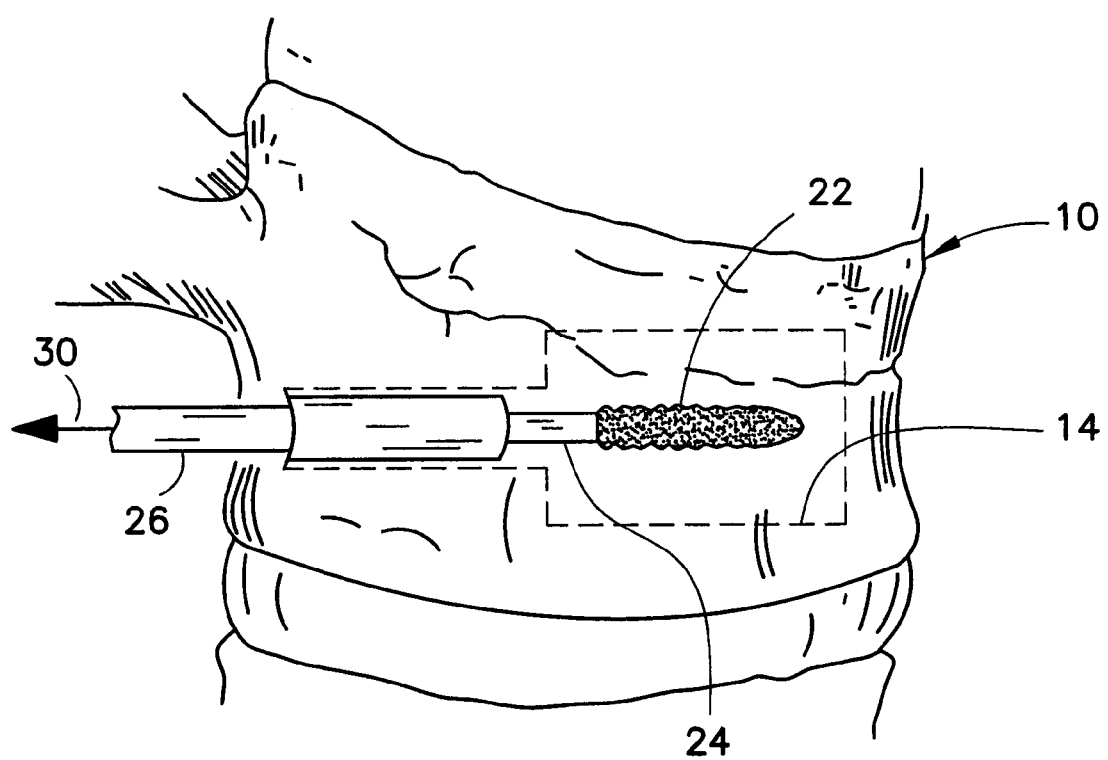
FIG. 5 is a view of a vertebral body with items shown in phantom view
Figure 6:
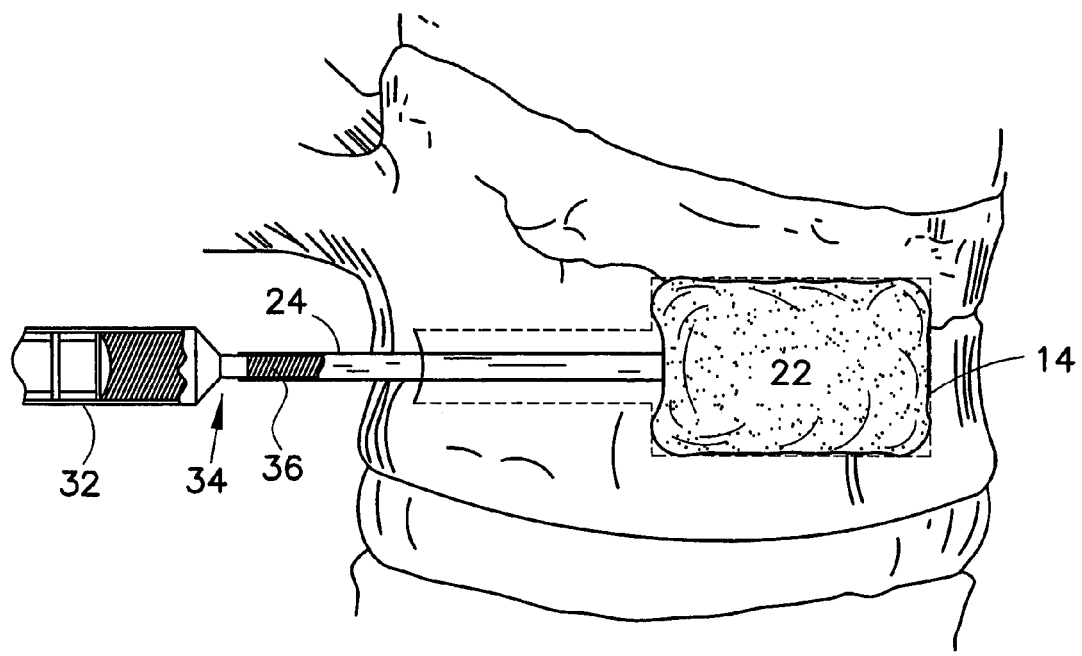
FIG. 6 is a view of a vertebral body with items shown in phantom view

Taken together FIG. 4 FIG. 5 and FIG. 6 represent steps in a method to stabilize a fractured vertebral body.

FIG. 4 shows a step in the method. In this drawing the container 22 is coupled to a fill tube 24 shown in phantom view. In this embodiment the container 22 is located at the distal end of a fill tube 24. The container 22 and fill tube 24 are carried together with the delivery tube 26. The motion arrow 28 indicates that the delivery tube 26 and fill tube 24 are being moved together into the surgically prepared cavity 14. The delivery tube 26 may be the same device that is used to deliver the cavity tools as discussed with reference to FIG. 1. Or the tube 26 may be a separate device inserted through an alternate access aperture.

FIG. 5 shows the deployment process step where the delivery tube 26 is retracted as indicated by motion arrow 30 while the fill tube 24 and the attached container 22 remain stationary in the vertebral body 10 cavity 14.

FIG. 6 shows the expansion of the container 22 within the cavity 14. The bone filler material 36 seen in phantom view has been loaded into the manually operated syringe 32 and the physician is injecting the material through the fill tube 24 into the container 22. The container 22 has unfurled and conformed to the shape of the cavity 14. The unconstrained shape of this container is generally cylindrical with spherical ends. This figure shows the deployment of the container in to a cavity which is substantially the same volume as the cavity 14. In this illustrative example the volume of the container is larger than the volume of the cavity and there is no stretching force applied to the impermeable container membrane.

The coupling 34 between the fill tube and the syringe 32 may be a conventional luer lock or other attachment device. Although a syringe is an effective filler delivery tool it is expected that physicians will use an alternative delivery system such as a an extruder rod inserted directly into the fill tube to displace bone filler into the container.

Figure 7:
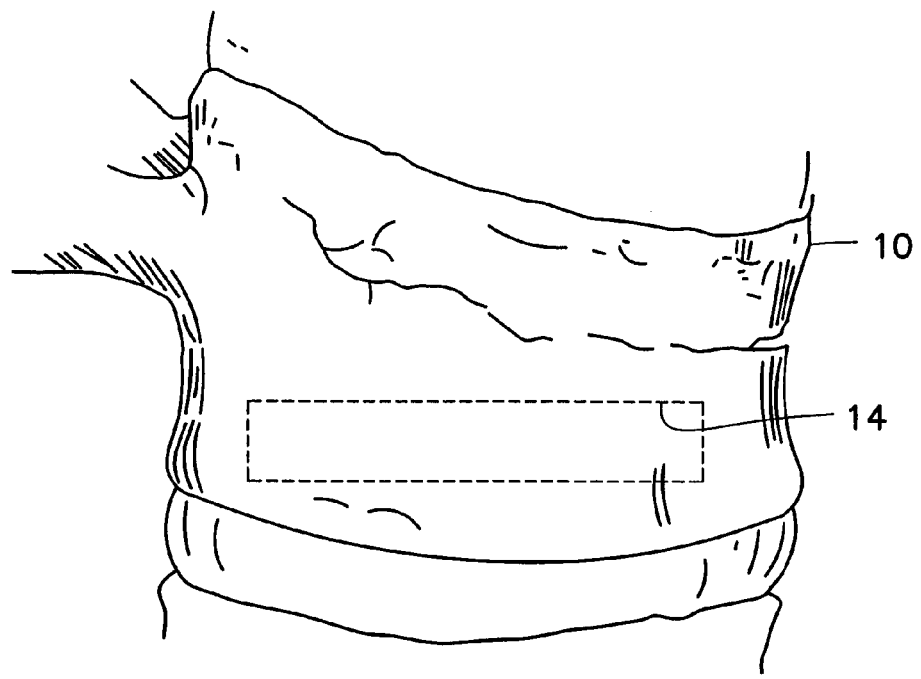
FIG. 7 is a view of a vertebral body with items shown in phantom view

FIG. 7 depicts the preliminary preparation of a cavity 14 in a collapsed vertebral body 10.

Figure 8:
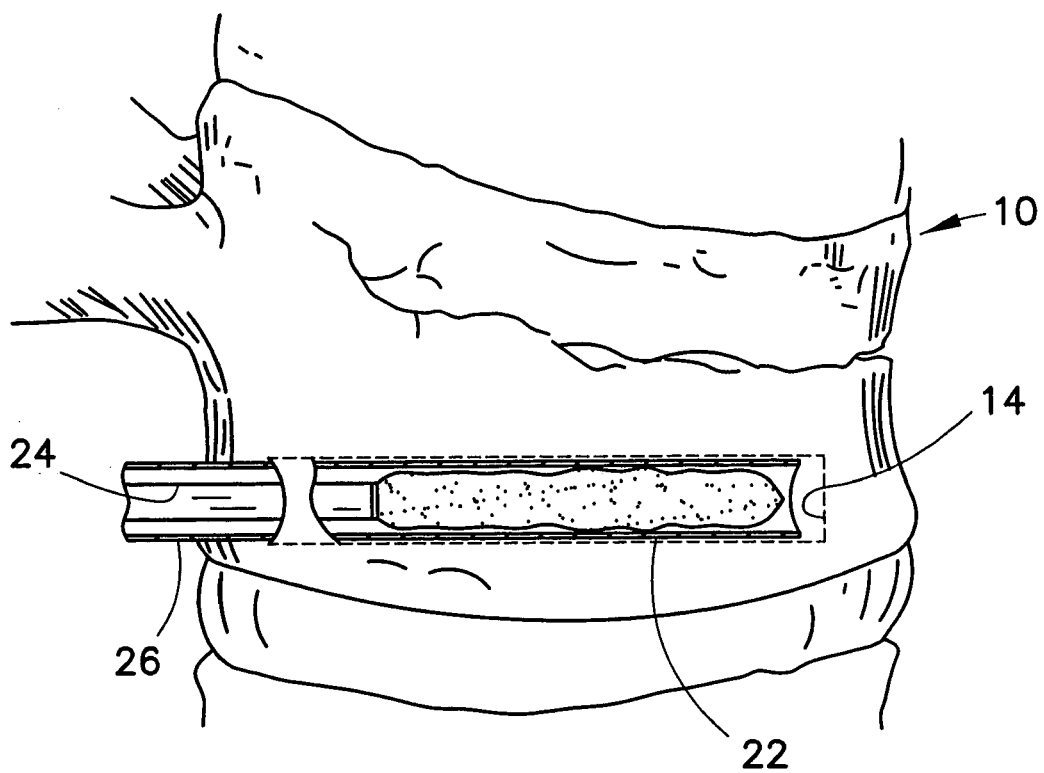
FIG. 8 is a view of a vertebral body with items shown in phantom view

FIG. 8 shows an introduction step in the hydraulic jacking process. In this illustration the container 22 and its attached fill tube 24 are inserted into the vertebral body 10 together with the delivery tube 26. The assembly is positioned in the cavity 14 proximate the end of the cavity. In this step care must be taken to prevent pressurizing the device within the pedicle.

Figure 9:
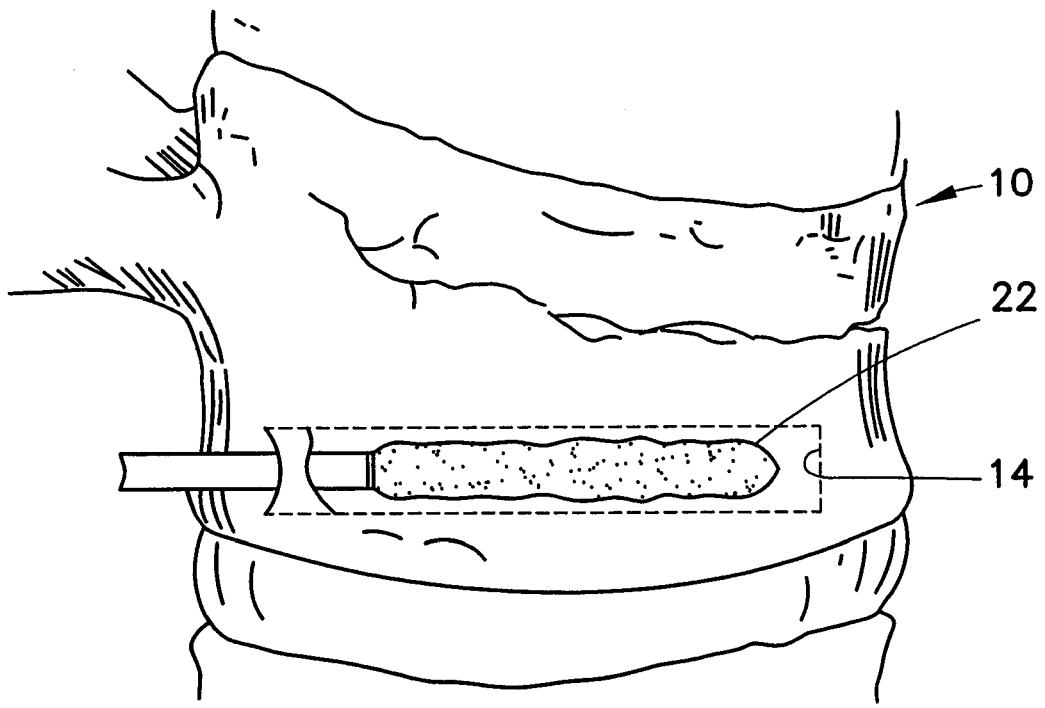
FIG. 9 is a view of a vertebral body with items shown in phantom view

FIG. 9 shows a deployment step in the process. In this illustration the container is fully deployed in the cavity 14 by withdrawing the delivery tube (not shown) from the fill tube leaving the container 22 exposed in the cavity 14.

Figure 10:
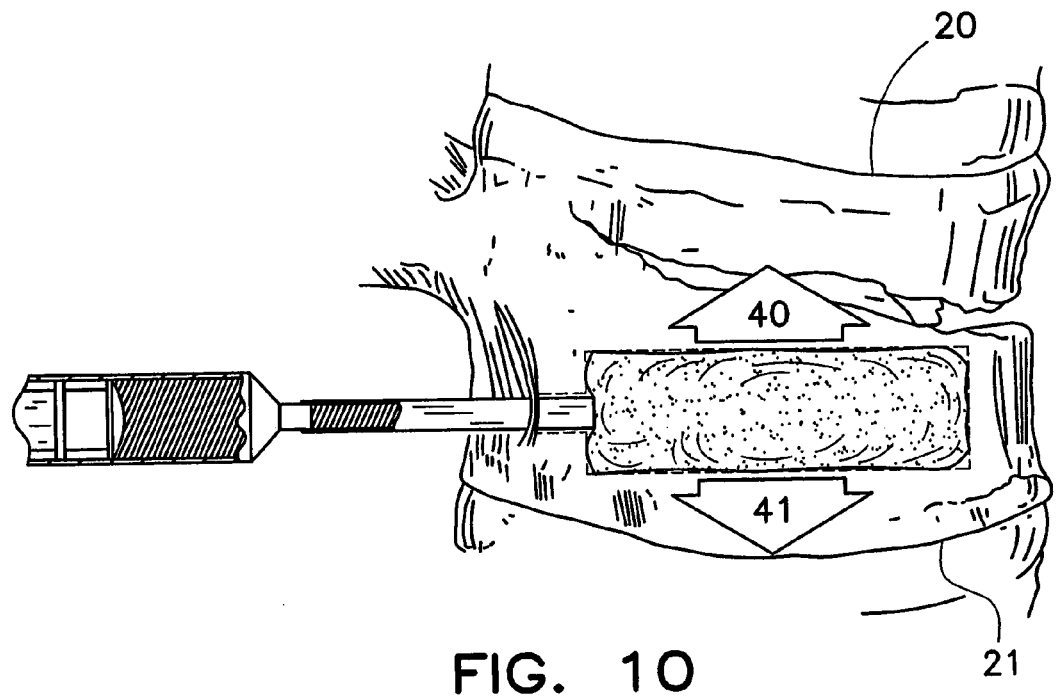
FIG. 10 is a view of a vertebral body with items shown in phantom view.

FIG. 10 shows an injection step in the process. The container 22 is filled through the fill tube 24 with a bone filler materials 36. The manual syringe 32 or other injection device injects the material at a sufficient pressure to create distraction forces shown in the figure a superior force 40 and inferior force 42. These forces are sufficient to move the endplate 20 and end plate 21 apart restoring height and angulation.

Figure 11:
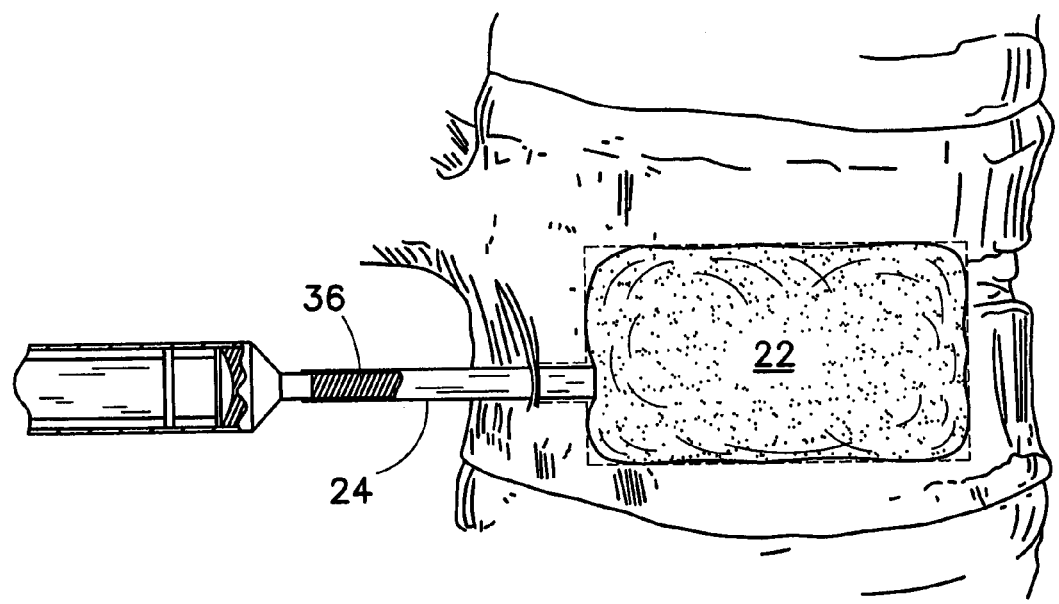
FIG. 11 is a view of a vertebral body with items shown in phantom view.

FIG. 11 shows a step of the process where an end point of the method is reached. Here the container 22 is completely filled and the original height of the vertebral body is restored. This end point can be determined in any of several ways. For example an inelastic fixed volume container can be used and the injecting process stopped when resistance is felt through the hydraulic connection with the container. An alternate approach is the injection of a fixed volume of bone filler into an oversized elastic or porous container 22. Also the physician may follow the injection under fluoroscopy and limit injection through observation of a real time image in combination with medical judgement. In this instance the container can be inelastic or elastic. The final step in the typical method will be to remove the fill tube 24 from the container 22. This step will typically be performed after the bone filler 36 material is "step up" and no longer in a low viscosity state.

These initial figures depict the stabilization method and the hydraulic jacking method performed with substantially cylindrical containers. The membranes in the examples have all been impermeable to the bone filler. In these process the container may be elastic or inelastic as may be desired by the physician.

The stabilization method may be performed with all of the container devices shown.

Figure 13:
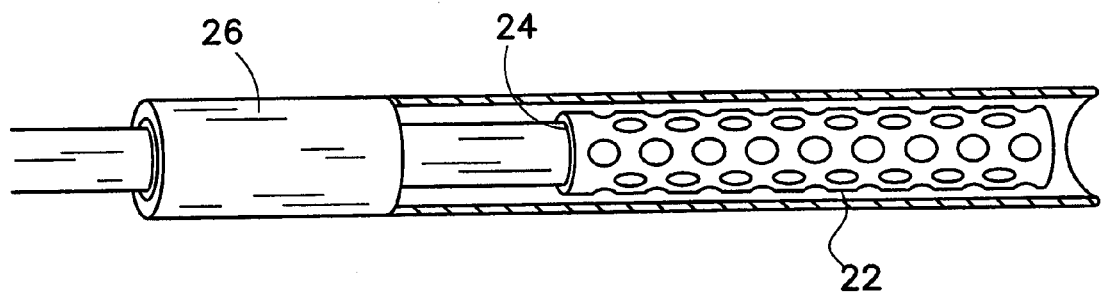
FIG. 13 is a view of an embodiment of a porous container.
Figure 14:
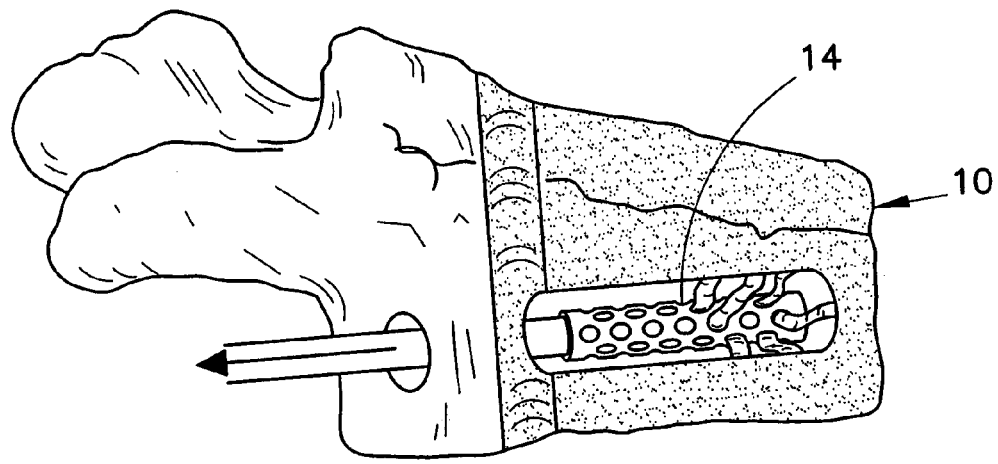
FIG. 14 is a view of a porous container in a cutaway vertebral body.

The hydraulic jacking method can be performed with the all of the container devices with the exception of FIG. 13 and FIG. 14.

Figure 12:
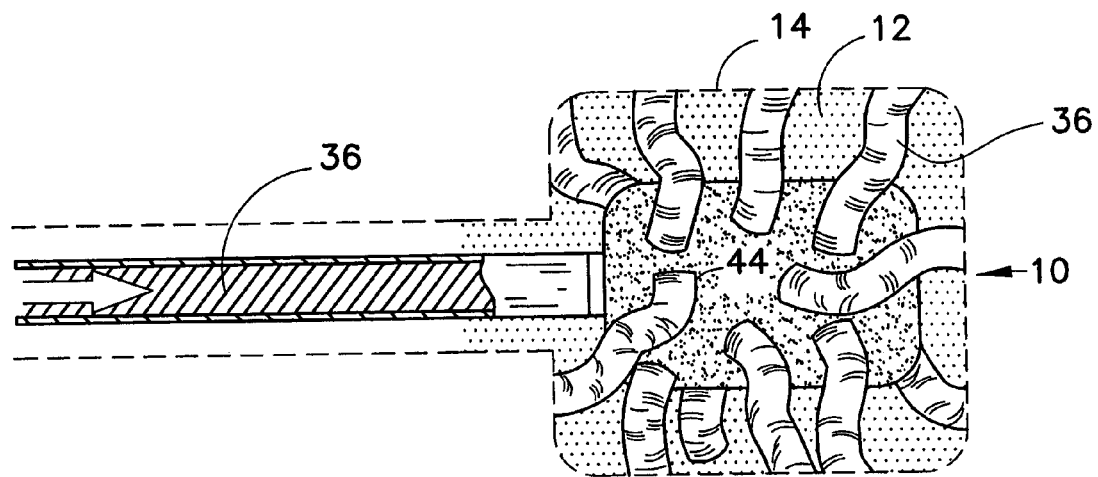
FIG. 12 is a view of an embodiment of a porous container in use.

FIG. 12 shows an alternate container 22 with a membrane perforated by a series of holes typified by hole 44. When placed in a vertebral body the bone filler 36 extrudes from the holes and interdigitates with the cancellous bone 12 inside the vertebral body 10. It is difficult to illustrate this process but the cavity 14 has a wall that is porous so the bone filler interdigitates with the cancellous bone matrix.

FIG. 13 shows a tubular fixed diameter form of the container 22 which can be used to control the delivery of bone filler to the cavity. The container 22 approximates the size and shape of the cavity, prior to bone filler injection. The holes in the device distribute the bone filler to locations next to the holes.

FIG. 14 shows the container of FIG. 13 in operation in a vertebral body 10.

One preferred method of use which can be performed with porous containers involves the injection of a first volume of relatively less viscous bone filler to promote interdigitation of the cancellous bone. Next a second injection of bone filler material with a different mechanical strength or chemical composition is injected and it "pushes" against the initial or primary injected material. This technique produces a gradient of strength and elasticity through the repaired bone which mimics the mechanical characteristics of the natural bone. The relatively small diameter of this device allow the set of apertures to distribute the various bone filler materials without moving the device during injection.

Another preferred method involves the same two stage injection process with a non-porous or impermeable container. In this instance there is negligible interdigitation but the gradient remains.

Figure 15:
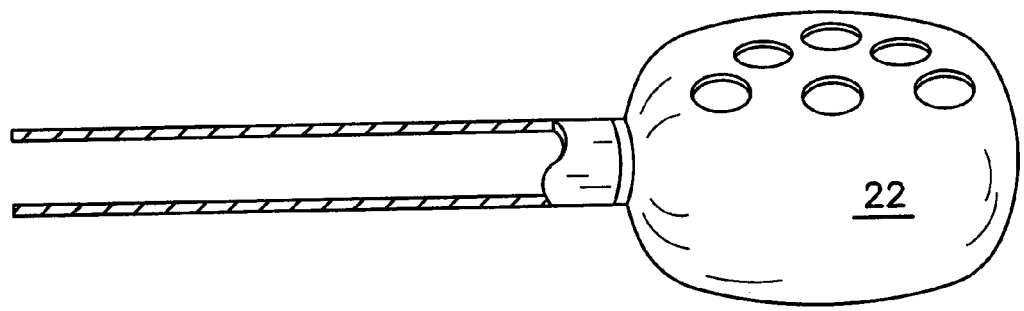
FIG. 15 is a view of a container in isolation.

FIG. 15 is a container with an asymmetrical distribution of holes so that the extrusion of bone filler occurs on one side of the container. This construction may allow the container to be moved within the vertebral body during injection of bone filler.

Figure 16:
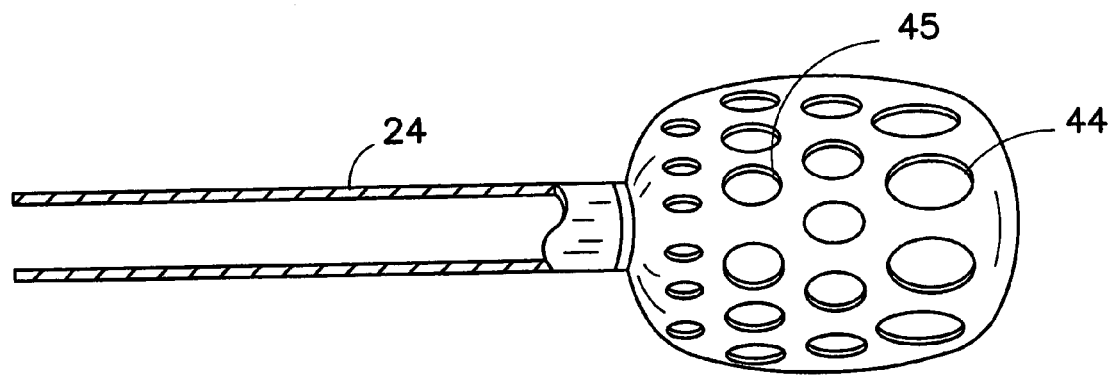
FIG. 16 is a view of a container in isolation.

FIG. 16 shows an asymmetrical container 22 where hole size and distribution vary over the surface of the membrane. For example hole 44 is larger than holes 45 which lie along the axis of the fill tube 24. This asymmetry provides physician control of the distribution and the flow of the bone filler materials into specific regions of the vertebral body.

Figure 17:
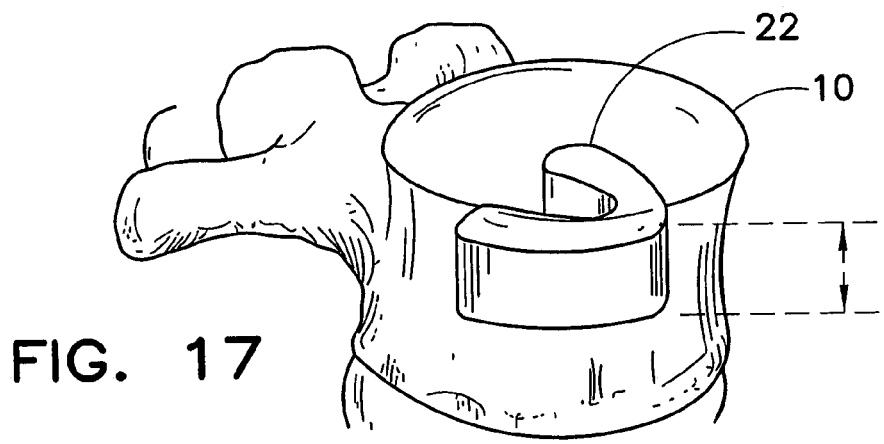
FIG. 17 is a perspective view of a container in a vertebral body.
Figure 18:
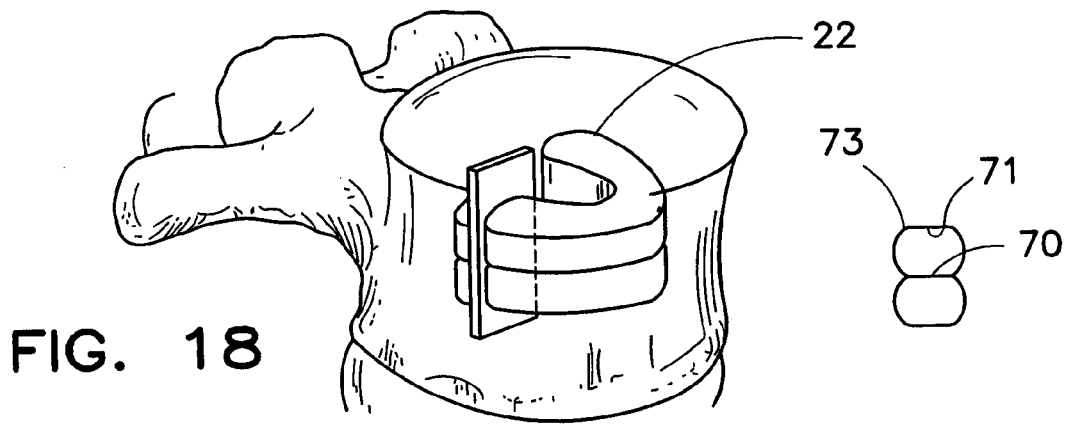
FIG. 18 is a perspective view of a container in a vertebral body.
Figure 19:
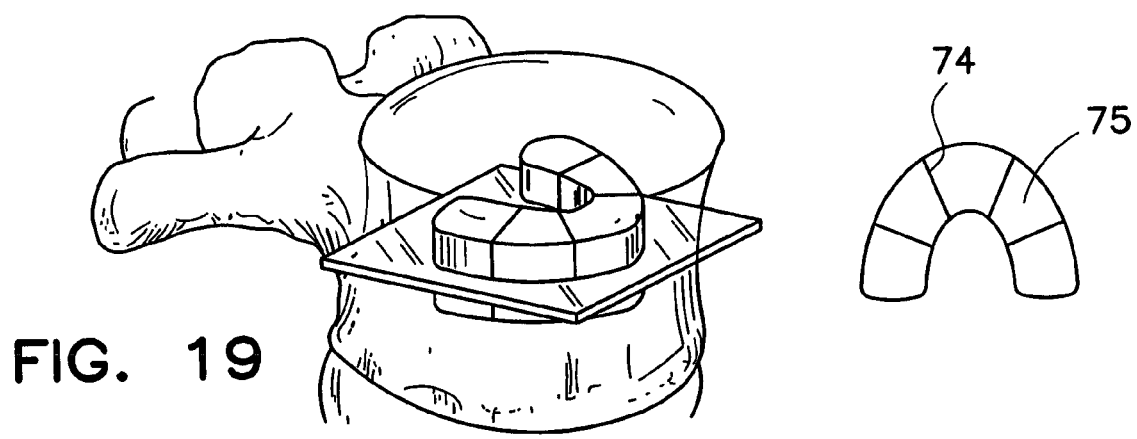
FIG. 19 is a perspective view of a container in a vertebral body.

FIG. 17, FIG. 18 and FIG. 19 should be considered together. This group of drawings depicts an alternate "horseshoe" shape for the construction for the container 22. In each instance the fill tube has been eliminated from the figure to improve clarity. However it should be understood that at least one fill tube is used with each container in these figures. All of the container devices depicted in FIG. 17 through FIG. 20 can be made of porous or non-porous membrane materials.

FIG. 17 is single chamber fixed volume device 22 which may expand to a nominal height in the vertebral body 10.

FIG. 18 is a segmented horseshoe shaped container 22 device with a horizontal rib 70 that divides the container into two separate structures. The inner of the membrane 71 may be continuous with this rib 70 or weep holes may be provided to facilitate flow of bone filler within the device. The exterior surface of the membrane 73 may be porous or impermeable to bone filler. In this embodiment the rib 70 will effectively limit the height achieved in the vertebral body.

FIG. 19 is multi-chambered device with several lateral compartments created by ribs typified by rib 74. In this embodiment the chambers typified by chamber 75 limit the horizontal extent of the growth of the container during the hydraulic jacking process.

Figure 20:
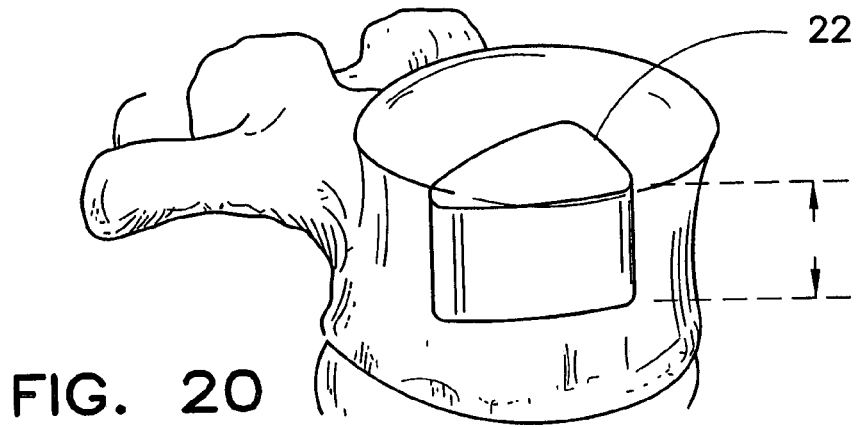
FIG. 20 is a perspective view of a container in a vertebral body.

FIG. 20 is single chamber fixed volume device 22 with a triangular "footprint".

Figure 21:
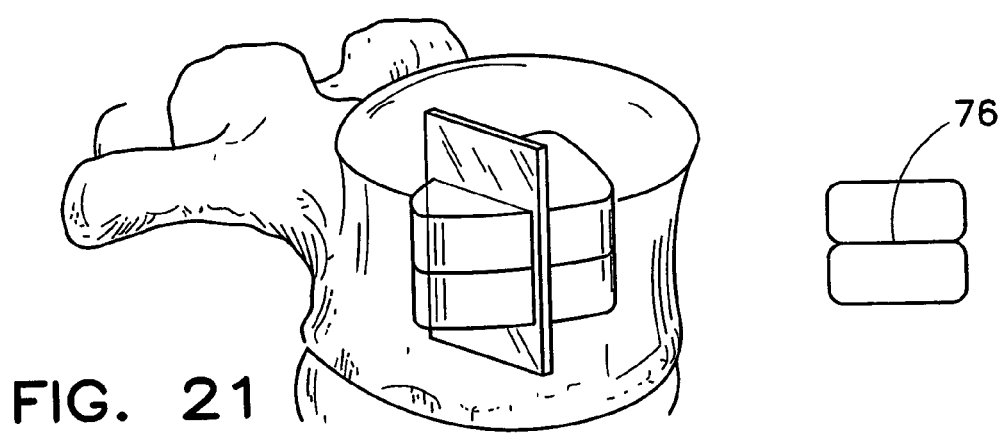
FIG. 21 is a perspective view of a container in a vertebral body

FIG. 21 is a segmented triangular device with a horizontal rib 76 defining two chambers.

Figure 22:
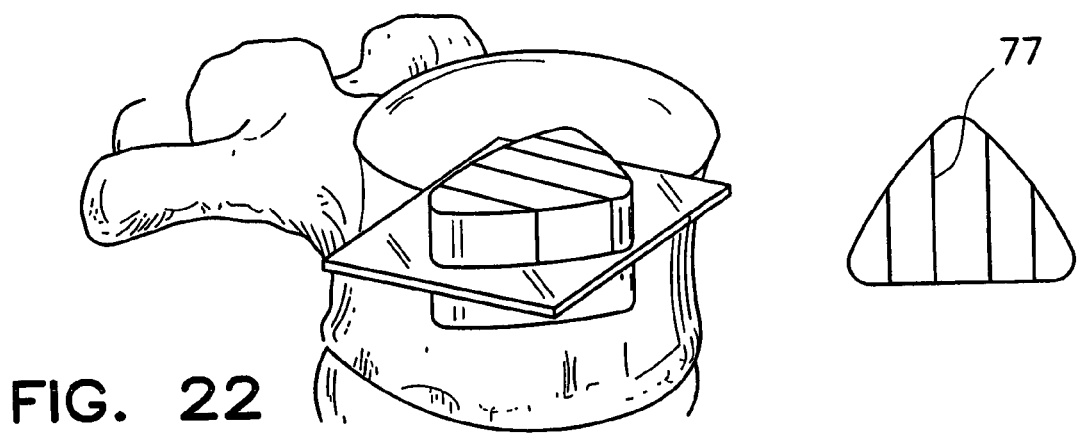
FIG. 22 is a perspective view of a container in a vertebral body

FIG. 22 is multi-chambered device with several lateral compartments created by ribs typified by rib 77.

Figure 23:
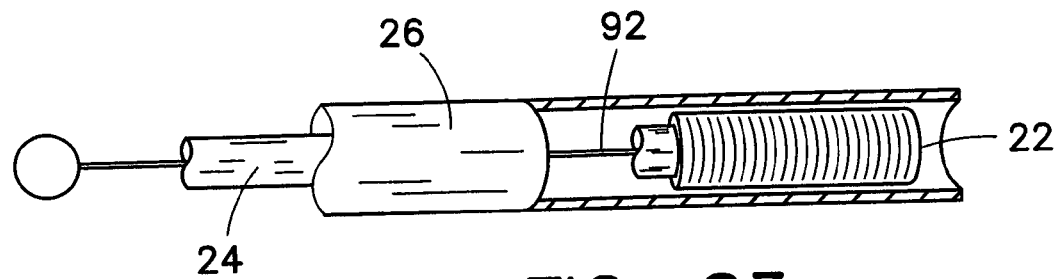
FIG. 23 is a view of a tubular container.

FIG. 23 shows an alternate tubular embodiment of a single chamber container 22 with a stylet 92 coupled to the most distal end of the container 22. This elongate tubular container is deployed by advancing the stylet 92 wire out of the delivery tube, which drags the container membrane out of the delivery tube 26 or the fill tube 24. In this device the container may be folded and placed entirely everted in the fill tube. This construction will allow the device to be safely delivered without the use of a delivery tube thereby maximizing the inner diameter of the fill tube.

Figure 24:
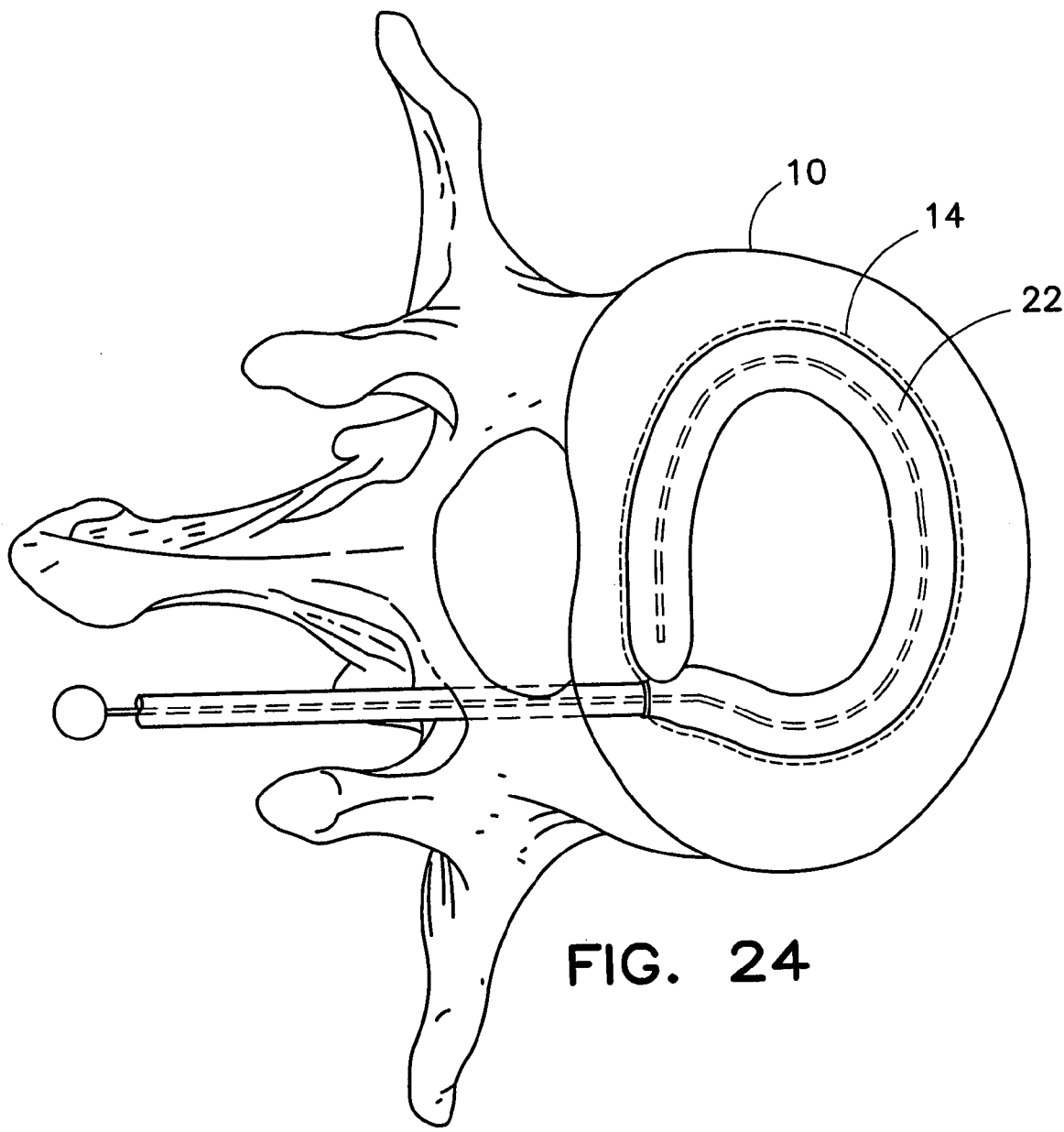
FIG. 24 is a view of a tubular container in use.

FIG. 24 shows the alternate tubular embodiment of the container in its partially filled configuration. In this illustration the vertebral body 10 has had an oval cavity 14 formed in the cancellous bone. The stylet 92 is used to force the container 22 along the outer wall path of the cavity 14 and it is then removed. Next bone filler material is injected through the fill tube and the annular ring tubular container is filled.

Figure 25:
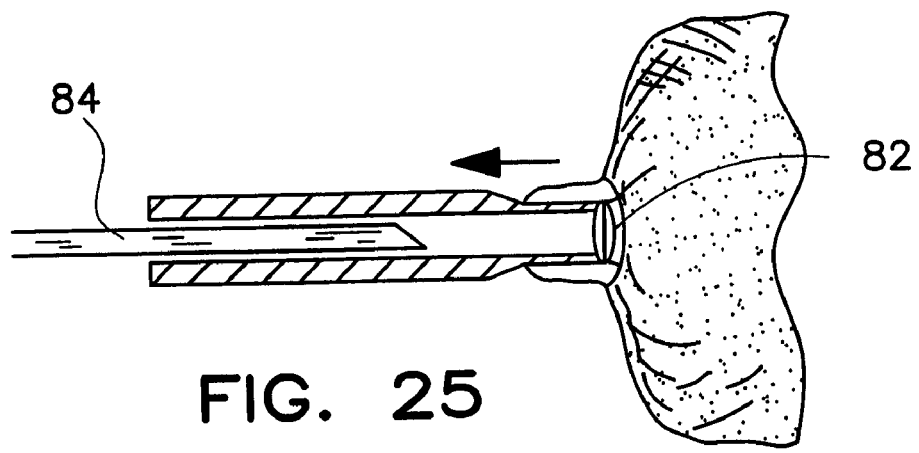
FIG. 25 is a view of a fill tube construction.

FIG. 25 shows a simple slip fit between the fill tube 24 and a complementary structure on the container 22. In this construction a septum 82 is used to fill the container 22 though a fill needle 84. One advantage of this construction is the septum seals the container and allows the container to seal while the bone filler hardens.

Figure 26:
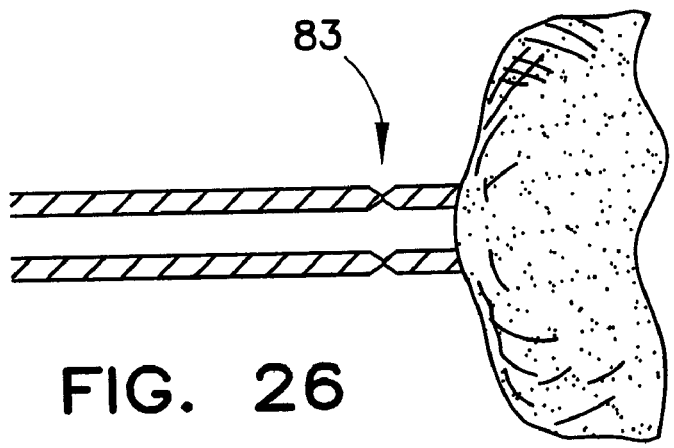
FIG. 26 is a view of a fill tube construction.

FIG. 26 shows are area or zone of weakness 83 in the fill tube 24 that preferentially breaks off to remove the fill tube from the container.

Figure 27:
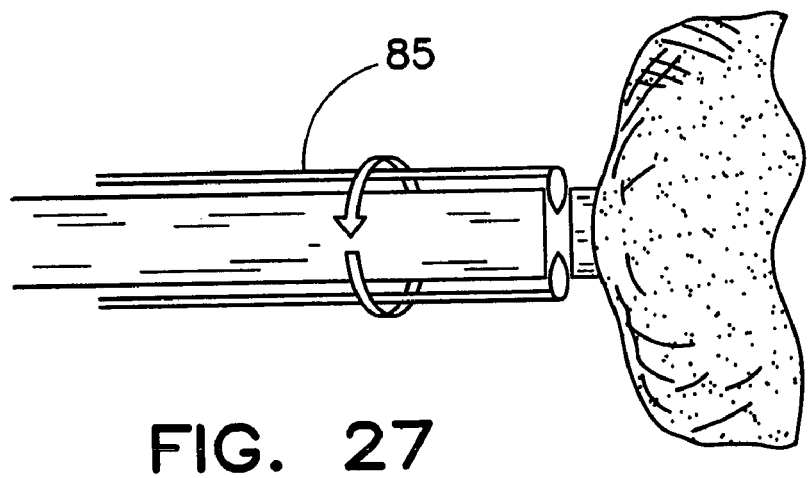
FIG. 27 is a view of a fill tube construction.

FIG. 27 the toothed member 85 circulates around the axis of the fill tube 24 and cuts of the fill tube away from the container after the bone filler has hardened.

Figure 28:
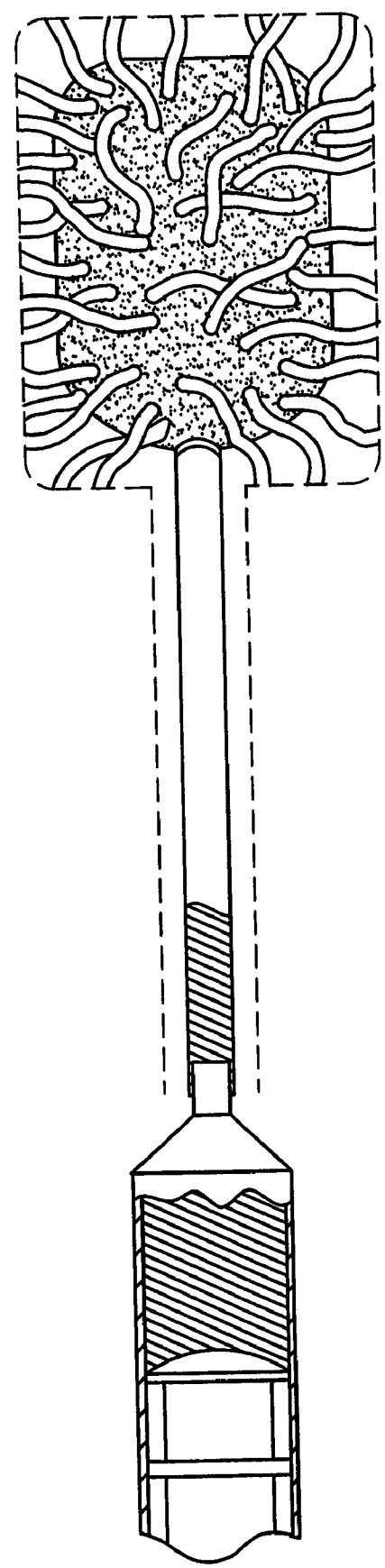
FIG. 28 is a view of an alternate porous container embodiment.

FIG. 28 shows the container formed as a porous woven membrane 90. In use the bone filler 36 will exude from the area between the woven fibers to permeate the cancellous bone. The woven mesh will produce the same effect as an elastic membrane.

Various materials may be used to make the container including, polyethylene Teflon, Gore-Tex, polybutylene terephathlate, polyethylene terephathalate glycol, urethane and urethane coated materials. The material or the construction can give rise to elastic or inelastic structures both of which are operable in the methods of the invention. The woven embodiments of the porous container may also be made from metal meshes or screens including titanium, elgiloy MP35 nitinol, stainless steel, or other bio-compatible metals.

Various bone fillers contemplated within the scope of this invention. Bone fillers are defined for this disclosure as any substance used to stabilize the bone and includes but is not limited to bone cement, human bone graft (allograft autograft), synthetic derived bone substitutes such as calcium phosphate and hydroxylapatite. Bone fillers may be supplemented with other biologically active materials including but not limited to collagen osteoinductive agents including bone morphogenic proteins. Other known ceramic based materials can be used as well. Other known bioresorbable polymers may be used as well.

Illustrative embodiments of the invention have been shown but numerous modifications may be made without departing from the scope of the invention which is defined by the appended claims.

What is claimed is:

1. A method of treating a vertebral bone having cancellous bone therewithin, comprising the steps of:
   inserting a porous container within the cancellous bone of the vertebral bone;
   injecting a first bone filler into said container; and
   injecting a second bone filler different from said first bone filler into said container,
   wherein said first bone filler is initially introduced into said container and wherein said second bone filler is then introduced into said container to push against said first bone filler until a portion of said first bone filler flows through the porous container and interdigitates with said cancellous bone of said vertebral bone.

2. The method of claim 1, wherein said first bone filler is selected to have a viscosity less than the viscosity of said second bone filler.

3. The method of claim 1, wherein said first bone filler is selected to have a chemical composition different from the chemical composition of said second bone filler.

4. The method of claim 1, wherein said first bone filler is selected to have a mechanical strength different from the mechanical strength of said second bone filler.

5. The method of claim 1, wherein said container is selected to be a woven mesh.

6. The method of claim 1, wherein said container is selected to be impermeable.

7. The method of claim 6, wherein said container is selected to be elastic.

8. The method of claim 6, wherein said container is selected to be inelastic.

9. The method of claim 1, wherein said first bone filler is selected to have a viscosity greater than the viscosity of said second bone filler.

* * * * *